(12) United States Patent
Pacetti

(10) Patent No.: US 8,945,663 B2
(45) Date of Patent: Feb. 3, 2015

(54) METHOD FOR BIOSTABLE INCLUSION OF A BIOBENEFICIAL AGENT ON AN OUTERMOST SURFACE OF AN IMPLANTABLE MEDICAL DEVICE

(75) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1603 days.

(21) Appl. No.: 12/108,440

(22) Filed: Apr. 23, 2008

(65) Prior Publication Data

US 2009/0269479 A1     Oct. 29, 2009

(51) Int. Cl.
| A61L 33/00 | (2006.01) |
| B05D 3/00 | (2006.01) |
| A61L 31/10 | (2006.01) |
| A61L 31/14 | (2006.01) |
| A61L 31/16 | (2006.01) |

(52) U.S. Cl.
CPC ............. *A61L 31/10* (2013.01); *A61L 31/14* (2013.01); *A61L 31/16* (2013.01); *A61L 2300/416* (2013.01); *A61L 2300/62* (2013.01); *A61L 2420/08* (2013.01)
USPC ........................................................ 427/2.24

(58) Field of Classification Search
CPC .......... A61L 31/10; A61L 31/16; A61L 27/34
USPC ........................................................ 427/2.24
See application file for complete search history.

(56) References Cited

U.S. PATENT DOCUMENTS 6,673,385 B1 *  1/2004  Ding et al. ................... 427/2.28
6,896,965 B1     5/2005  Hossainy

FOREIGN PATENT DOCUMENTS

EP        1 504 775         2/2005
WO     WO 03/028780         4/2003

OTHER PUBLICATIONS

International Search Report for PCT/US2009/041292, mailed Jun. 2, 2010, 6 pgs.
"Coating at the Speed of Light, Processing Cycle Times for Profitability", SurModics, Inc., 4 pgs. 2004.
"PhotoLink® Technology-Photochemistry" SurModics, Inc., 1 pg. downloaded www.surmodics.com/pageDetail.aspx, Mar. 24, 2008.

* cited by examiner

*Primary Examiner* — Bijan Ahvazi
*Assistant Examiner* — Atnaf Admasu
(74) *Attorney, Agent, or Firm* — Sqire Patton Boggs (US) LLP

(57) ABSTRACT

The current invention is directed to a method of protecting UV or visible light sensitive drugs from the effects of UV or visible radiation used to form covalent bonds between a biobeneficial material and the outermost surface of an implantable medical device in order to lessen the foreign body response to the device.

16 Claims, No Drawings

METHOD FOR BIOSTABLE INCLUSION OF A BIOBENEFICIAL AGENT ON AN OUTERMOST SURFACE OF AN IMPLANTABLE MEDICAL DEVICE

FIELD OF THE INVENTION

The current invention relates to coatings for implantable medical devices having a biobenefical agent biostably attached to the surface of an outermost coating of the device. In particular, the implantable medical device is a drug eluting stent (DES).

BACKGROUND

When using in-dwelling medical devices, a common problem is the relative non-biocompatibility of the device which may result in, for instance, inflammation, thrombus formation and/or protein fouling, i.e., precipitation and denaturization on the surface of the device. To ameliorate these and other after-effects biobeneficial materials that present a surface that is more in tune with the natural surroundings at the site of device incorporation and thereby lessen a patient's normal foreign body response are often included on the outermost surface of the device, be it the bare device or a coating thereon. Being at the outermost level of the device, however, virtually insures that the biobeneficial material will elute from, be washed or abraded off of or otherwise will be removed from the outer surface of the device. To avoid such result, it is desirable to chemically attach the biobeneficial material to the outer surface of the device such that it cannot be physically removed, at least not without extraordinary effort that would essentially result in the destruction of the coating on the device.

One means of accomplishing the bonding of the biobeneficial material to the outer surface of a device is to photochemically create a covalent bond between the material and the surface. A commercial means for effecting such bonding is SurModics' Photolink® technology. Photolink® is used to conjugate surface active molecules to the outermost surface of medical devices. A photolyzable group is chemically conjugated to the material of interest, the conjugate is applied to the surface, which must include an abstractable hydrogen atom, and the device is subjected to UV or visible radiation. The radiation initiates a cascade of events that ultimately results in the formation of a covalent bond between the photolyzable group and the device surface. Since the biobeneficial material is in turn also covalently bonded to the photolyzable group, the result is that the material is securely attached to the surface of the device where it can then carry out its intended purpose in vivo without fear of its being lost from the surface of the device.

A problem arises, however, when the technique is to be applied to a drug-eluting stent or other such drug-containing device in that many drugs are photosensitive to the same radiation used to carry out the photolytic reaction between the material and the surface of the device. This photosensitivity may result in the degradation or inactivation of the drug rendering the device useless as a means of drug delivery.

What is needed is a method of protecting radiation sensitive drugs during the formation of the links between a biobeneficial material and the surface of a drug-carrying device. The current invention provides such a method.

SUMMARY

Thus, in one aspect the current invention relates to a method comprising: providing an implantable medical device comprising a device body; optionally disposing a primer layer over an exposed surface of the device body; disposing a drug reservoir layer over an exposed surface of the device body or, if opted for, over the primer layer, wherein:
the drug reservoir layer comprises:
a first polymer that includes at least one constitutional unit having at least one carbon-hydrogen bond capable of radical formation, a UV and/or visible light sensitive therapeutic agent and optionally, a UV and/or visible light blocker that absorbs UV and/or visible radiation at the wavelength(s) to which the therapeutic agent is sensitive;
optionally disposing a topcoat layer over the drug reservoir layer wherein the topcoat layer comprises a second polymer, which may be the same as or different than the first polymer; having at least one constitutional unit having at least one carbon-hydrogen bond capable of radical formation, wherein
if the topcoat layer is opted for it optionally further comprises a UV and/or visible light blocker that absorbs UV and/or visible radiation at the wavelength(s) to which the therapeutic agent is sensitive;
disposing a UV or visible light active biobeneficial agent over the drug reservoir layer or, if opted for, over the topcoat layer; and,
curing the device with UV or visible radiation.

In an aspect of this invention, the topcoat layer is not opted for and the surface of the drug reservoir layer is cleaned prior to disposition of the UV or visible light active biobeneficial agent.

In an aspect of this invention, cleaning the drug reservoir layer comprises washing the surface of the drug reservoir layer with a solvent for the therapeutic agent followed immediately by drying.

In an aspect of this invention, cleaning the drug reservoir layer comprises subjecting the surface of the drug reservoir layer to an inert gas plasma.

In an aspect of this invention the therapeutic agent is encapsulated in a micro- or nano-particle comprising the UV or visible light blocker.

In an aspect of this invention, the UV or visible light active biobeneficial agent comprises a biobeneficial agent to which a UV or visible light radical-forming entity has been covalently bonded.

In an aspect of this invention, the polymer constitutional unit comprises vinylidene fluoride.

In an aspect of this invention, the polymer comprises poly (vinylidene fluoride-co-hexafluoropropylene).

In an aspect of this invention the primer layer and the topcoat layer are not opted for.

In an aspect of this invention, the UV and/or visible light sensitive therapeutic agent comprises an olimus drug.

In an aspect of this invention, the olimus drug is selected from the group consisting of sirolimus, everolimus 40-O-(3-hydroxy)propylrapamycin, 40-[O-2-(2-hydroxy)ethoxy]ethylrapamycin, zotarolimus, 40-O-tetrazolerapamycin, 40-epi-(N1-tetrazole)rapamycin, biolimus A9,, deforolimus, temsirolimus and AP23572, (Ariad Pharmaceuticals).

In an aspect of this invention, the UV or visible light blocker is selected from the group consisting of carotene, tyrosine, phenyl alanine, dihydroxyphenylalanine, desaminotyrosine, vitamin A, a B vitamin, vitamin E, squalene, an aromatic steroid, retinoic acid, a tocopherol, retinol, retinol ester, carotinoids, anthocyanines, acetylsalicylic acid, benzoic acid, a benzoic acid ester, BHT, BHA, eosin, fluorescein, melanin, zinc oxide, titanium oxide, a metal and carbon black.

In an aspect of this invention, the UV or visible light active biobeneficial agent is selected from the group consisting of UV or visible light active poly(ethylene glycol), poly(propylene glycol); poly(ethylene oxide-co-lactic acid); poly(ethylene oxide), poly(propylene oxide); polyphosphazenes, phosphoryl choline, choline, poly(hydroxyethyl methacrylate), poly(hydroxypropyl methacrylate), poly(hydroxypropylmethacrylamide), poly(ethylene glycol) acrylate, 2-methacryloyloxyethylphosphorylcholine, n-vinyl pyrrolidone; poly(methacrylic acid), poly(acrylic acid), poly(alkoxymethacrylate), poly(alkoxyacrylate), poly(3-trimethylsilylpropyl methacrylate); poly(styrene-co-ethyene glycol), poly(isobutylene-co-ethylene glycol), poly(caprolactone-co-ethylene glycol), poly(lactide-co-ethyene glycol), poly(methyl methacrylate-co-ethylene glycol), poly(dimethylsiloxane-co-ethylene glycol), poly(vinylidene fluoride-co-ethylene glycol), poly(propylene oxide-co-ethylene glycol), poly(tetramethylene glycol), hydroxy functionalized poly(vinyl pyrrolidone), poly(ethylene glycol-block-butylene terephthalate), fibrin, fibrinogen, cellulose, starch, collagen, dextran, dextrin, hyaluronic acid, heparin, glycosaminoglycan, a polysaccharide, elastin, chitosan, alginate and combinations thereof.

In an aspect of this invention, the UV or visible light radical-forming entity comprises an aryl ketone.

In an aspect of this invention, the aryl ketone is selected from the group consisting of acetophenone, benzophenone, anthraquinone, anthrone, an anthrone-like heterocycle, a conjugated cyclic diketone, derivatives of any of the foregoing and combinations of any of the foregoing.

In an aspect of this invention the implantable medical device is a stent.

DETAILED DESCRIPTION

As used herein, the singular includes the plural and visa versa unless expressly stated to be otherwise. That is, "a" and "the" refer to one or more of whatever the word modifies. For example, "a therapeutic agent" includes one such agent, two such agents, etc. Likewise, "the layer" may refer to one, two or more layers and "the polymer" may mean one polymer or a plurality of polymers. By the same token, words such as, without limitation, "layers" and "polymers" would refer to one layer or polymer as well as to a plurality of layers or polymers unless, again, it is expressly stated or obvious from the context that such is not intended.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, patent foramen ovule closure devices and cerebrospinal fluid shunts.

An implantable medical device specifically designed and intended solely for the localized delivery of a therapeutic agent is within the scope of this invention.

As used herein, "device body" refers to a fully-formed usable implantable medical device with an outer surface to which no coating or layer of material different from that of which the device itself is manufactured has been applied. A common example of a "device body" is a BMS, i.e., a bare metal stent, which, as the name implies, is a fully-formed usable stent that has not been coated with a layer of any material different from the metal of which it is made on any surface that is in contact with bodily tissue or fluids. Of course, device body refers not only to BMSs but to any uncoated device regardless of what it is made of.

By "exposed surface" is meant any surface of a device body, however spatially oriented, that is in contact with bodily tissue or fluids.

Implantable medical devices made of virtually any material, i.e., materials presently known to be useful for the manufacture of implantable medical devices and materials that may be found to be so in the future, may be used with a coating of this invention. For example, without limitation, an implantable medical device useful with this invention may be made of one or more biocompatible metals or alloys thereof including, but not limited to, cobalt-chromium alloy (ELGILOY, L-605), cobalt-nickel alloy (MP-35N), 316L stainless steel, high nitrogen stainless steel, e.g., BIODUR 108,, nickel-titanium alloy (NITINOL), tantalum, platinum, tungsten-niobium-tantalum alloy, platinum-iridium alloy, gold and combinations thereof.

Implantable medical devices may also be made of polymers that are biocompatible and biostable or biodegradable, the latter term including bioabsorbable and/or bioerodable.

As used herein, "biocompatible" refers to a polymer that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

Among useful biocompatible, relatively biostable polymers are, without limitation polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biocompatible, biodegradable polymers may also be used to fabricate an implantable medical device useful with this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyhydroxyacids, polyhydroxyalkanoates, polyanhydrides, polyesters, polyorthoesters, polyamino acids, polyoxymethylenes, poly(ester-amides) and polyimides.

Blends and copolymers of the above polymers may also be used and are within the scope of this invention. Based on the disclosures herein, those skilled in the art will recognize those implantable medical devices and those materials from which they may be fabricated that will be useful with the coatings of this invention. At present, preferred implantable medical devices for use with the coatings of this invention are stents.

A stent refers generally to any device used to hold tissue in place in a patient's body. Particularly useful stents, however, are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

In addition to the above uses, stents may also be employed for the localized delivery of therapeutic agents to specific treatment sites in a patient's body. In fact, therapeutic agent delivery may be the sole purpose of the stent or the stent may be primarily intended for another use such as those discussed above with drug delivery providing an ancillary benefit.

A stent used for patency maintenance is usually delivered to the target site in a compressed state and then expanded to fit the vessel into which it has been inserted. Once at a target location, a stent may be self-expandable or balloon expandable. In any event, due to the expansion of the stent, any coating thereon must be flexible and capable of elongation.

As used herein, "optional" and "optionally" mean that the element modified by the term may or may not be present. For example, without limitation, a device body (db) that has coated on it an "optional" primer layer (pl), a drug reservoir layer (dr) and an "optional" top-coat layer (tc) refers, without limitation, to any of the following devices: db +dr; db+pl+dr; db+pl+dr+tc; and db+dr+tc.

As used herein, a "primer layer" refers to a coating consisting of a polymer or blend of polymers that exhibit good adhesion characteristics with regard to the material of which the device body is manufactured and good adhesion characteristic with regard to whatever material is to be coated on the device body. Thus, a primer layer serves as an adhesive intermediary layer between a device body and materials to be carried by the device body and is, therefore, applied directly to the device body. Examples without limitation, of primers include poly(ethylene-co-vinyl alcohol), acrylate polymers and methacrylate polymers with poly(n-butyl methacrylate) being a presently preferred primer.

As use herein, a layer that is described as being "disposed over" or a method described as "disposing . . . over" an indicated substrate, e.g., without limitation, a device body or another layer, refers to a relatively thin coating of a material applied, preferably at present, directly to essentially the entire exposed surface of the indicated substrate. "Disposed over" may, however, also refer to the application of the thin layer of material to an intervening layer that has been applied to the substrate, wherein the material is applied in such a manner that, were the intervening layer not present, the material would cover substantially the entire exposed surface of the substrate.

As used herein, "drug reservoir layer" refers to a layer of a polymer or a blend of polymers that has dispersed within its three-dimensional structure one or more therapeutic agents. A polymeric drug reservoir layer is designed such that, by one mechanism or another, e.g., without limitation, by elution, diffusion, or as the result of biodegradation of the polymer, the therapeutic substance is released from the layer into the surrounding environment.

As used herein, a "topcoat layer" refers to an outermost layer, that is, a layer that is in contact with the external environment and that is coated over all other layers. The topcoat layer may be applied to control release of the therapeutic agent from the underlying reservoir layer, to provide better hydrophilicity to the device, to better lubricate the device or merely as a physical protectant of the underlying layers. The topcoat layer, however, may also contain therapeutic agents, in particular if the treatment protocol being employed calls for essentially immediate release of one or more therapeutic agent (these being included in the topcoat layer) followed by the controlled release of another therapeutic agent or agents over a longer period of time. If the topcoat layer does contain a drug and if that drug is UV sensitive at the working wavelengths for diradical and covalent bond formation, the techniques disclosed herein for protecting drugs in the drug reservoir layer may be applied similarly to the topcoat layer.

As used herein, "therapeutic agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, the terms "drug" and "therapeutic agent" are used interchangeably.

As used herein, a "UV or visible light sensitive therapeutic agent" refers to a therapeutic agent that, when exposed to UV or visible light radiation is degraded or converted to a non-therapeutically effective entity that may entail, without limitation, a conformational change, a stereoisomer change or an actual chemical structure change. By "non-therapeutically effective" is meant that the agent no longer is capable of performing the biochemical functional it is selected to perform. While a therapeutic agent may be susceptible to a spectrum of UV and/or visible light wavelengths, generally there is one, perhaps two specific wavelengths to which the agent is most susceptible and which are capable of most rapidly causing the inactivation or degradation of the agent so that it is no longer a therapeutically effective entity.

Examples of classes and specific examples of therapeutic agents that are known, suspected or may be shown to be UV-sensitive include, without limitation, synthetic inorganic and organic compounds, proteins and peptides, polysaccharides and other sugars, lipids, DNA and RNA nucleic acid sequences including siRNA, antisense oligonucleotides, antibodies, receptor ligands, enzymes, adhesion peptides, blood clot agents such as streptokinase and tissue plasminogen activator, antigens, hormones, growth factors, ribozymes, retroviral vectors, paclitaxel, docetaxel, methotrexate, azathioprine, vincristine, vinblastine, fluorouracil, doxorubicin hydrochloride, mitomycin, antiplatelet compounds, anticoagulants, antifibrin, antithrombins such as sodium heparin, low molecular weight heparins, heparinoids, hirudin, argatroban, forskolin, vapiprost, curcumin, fingolimandod (FTY-720), prostacyclin, prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä, calcium channel blockers such as nifedipine, colchicine, fibroblast growth factor (FGF) antagonists, fish oil (omega 3-fatty acid), histamine antagonists, lovastatin, monoclonal antibodies, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, estradiol, anticancer agents, dietary supplements such as vitamins, anti-inflammatory agents such as aspirin, tacrolimus, dexamethasone and clobetasol, cytostatic substances such as angiopeptin, angiotensin converting enzyme inhibitors such as captopril, cilazapril or lisinopril, antiallergic agents is permirolast potassium, alpha-interferon, bioactive RGD, and genetically engineered epithelial cells.

A presently preferred class of therapeutic agents is the "olimus" drugs, which includes, without limitation rapamycin (sirolimus), 40-O-(2-hydroxyethyl)rapamycin (everolimus), 40-O-(3-hydroxypropyl)rapamycin, 40-O-(2-hydroxyethyoxy)-ethylrapamycin, 40-O-tetrazolylrapamycin (zotarolimus, ABT-578), 40-epi-(N1-tetrazole-rapamycin, biolimus, 40-O-[2-(2-hydroxy)ethoxy]ethyl-rapamycin, deforolimus, temsirolimus and AP23572, (Ariad Phamaceuticals. Particularly preferred at present is everolimus, which is known to be UV-sensitive at 277, nm.

As used herein, a "UV or visible light blocker" refers to a chemical entity that absorbs UV or visible light radiation, in particular at the wave-lengths to which the therapeutic agent is most susceptible although it may also absorb over a band of wavelengths to further protect the therapeutic agent. With regard to everolimus, a presently preferred therapeutic agent, it absorbs UV radiation particularly strongly at 277, nm. Thus, to avoid a detrimental effect on everolimus, a UV-blocker that absorbs UV at 277, nm would be desired. A blocker that absorbs UV radiation in a band of frequencies that includes 277, nm would be even more desirable.

A "biobeneficial" agent is one that beneficially affects an implantable medical device by, for example, reducing the tendency of the device to protein foul, increasing the hemocompatibility of the device, and/or enhancing the non-thrombogenic, non-inflammatory, non-cytotoxic, non-hemolytic, etc. characteristics of the device. For the puposes of this invention the biobeneficial agent is located on the outermost surface of a device be it the drug reservoir layer or a topcoat layer.

Some representative biobeneficial agents include, but are not limited to, polyethers such as poly(ethylene glycol) (PEG) and poly(propylene glycol); copoly(ether-esters) such as poly(ethylene oxide-co-lactic acid); polyalkylene oxides such as poly(ethylene oxide) and poly(propylene oxide); polyphosphazenes, phosphoryl choline, choline, polymers and co-polymers of hydroxyl bearing monomers such as hydroxyethyl methacrylate, hydroxypropyl methacrylate, hydroxypropylmethacrylamide, poly(ethylene glycol) acrylate, 2-methacryloyloxyethyl phosphorylcholine (MPC) and n-vinyl pyrrolidone (VP); carboxylic acid bearing monomers such as methacrylic acid, acrylic acid, alkoxymethacrylate, alkoxyacrylate, and 3-trimethylsilylpropyl methacrylate; poly(styrene-co-ethylene glycol), poly(isobutylene-co-ethylene glycol), poly(caprolactone-co-ethylene glycol), poly(lactide-do-ethylene glycol), poly(methyl methacrylate-co-ethylene glycol), poly(dimethylsiloxane-co-ethylene glycol), poly(vinylidene fluoride-co-ethylene glycol), poly(propylene oxide-co-ethylene glycol), poly(tetramethylene glycol), hydroxy functionalized poly(vinyl pyrrolidone), poly(ethylene glycol-co-butylene terephthalate); biomolecules such as fibrin, fibrinogen, cellulose, starch, collagen, dextran, dextrin, hyaluronic acid, heparin, glycosamino glycan, polysaccharides, elastin, chitosan, alginate, silicones and combinations thereof.

As used herein, "UV or visible light active biobeneficial agent" refers to a biobeneficial agent to which has been covalently bonded a moiety that, when exposed to a particular wavelength of UV or visible light radiation, absorbs energy and is raised to an excited quantum state that results in the formation of radical species. When this occurs at the interface of the UV or visible light active beneficial agent and the surface of the implantable medical device, a cascade of events ensues that ultimately results in the formation of a covalent bond between the moiety and the surface of the implantable medical device.

A "UV or visible light radical-forming entity" refers to a molecule that, on exposure to a predisposed wavelength of UV radiation, participates in the above reaction sequence. The predisposed UV or visible light wavelength at which the radical-forming entity will perform its function may overlap with the UV or visible light sensitive wavelengths of the therapeutic agent in which case it may be necessary to include a UV or visible light blocker in the drug reservoir layer. In the alternative, a UV or visible light radical-forming entity that operates at a wavelength sufficiently outside that of therapeutic agent sensitivity may be used in which case the UV or visible light blocker may be excluded and the source of UV or visible light energy selected so as to avoid the sensitive wavelength(s) of the therapeutic agent. For example, with regard to the presently preferred therapeutic agent of this invention, everolimus, a radical-forming entity that is photolyzable, i.e. activated, at a wavelength greater than 277, nm may be used. This can be combined with use of a UV source from which only a small amount of radiation at or near 277, nm may be used. For example, without limitation, a UV source that emits less than 10%, preferably less than 1% and most preferably at present less than 0.1% of its total intensity or power at wavelengths less than 300, nm may be used. With regard to everolimus, while its maximum absorbance is at 277, nm, radiation extending to about 500, nm is capable of degrading the compound. Therefore a UV light source that emits less than 10%, preferably less than 1% and most preferably at present less than 0.1% of its total intensity or power at wavelengths up to about 500 nm may be used.

An example, without limitation, of UV radical-forming entities is the aryl ketones. As used herein an "aryl ketone" refers to a ketone having the chemical structure R-aryl-C(=O)-aryl-R', wherein R and R' may be any manner of substituent known to those skilled in the art, the purpose of the R groups being primarily to modify the UV wavelength at which the molecule absorbs UV energy and is transformed to its activated singlet state. "Aryl" refers simply to a ring or multi-ring molecule that includes a fully delocalized pi-electron system around the entire ring.

With regard to everolimus, the drug is also somewhat susceptible to oxidative degradation and simultaneous exposure to UV radiation may exacerbate this effect. Thus, another therapeutic agent protective technique that may be used is to carry out the curing step in the absence of oxygen, which may be accomplished by curing in a vacuum or an inert atmosphere such as nitrogen or argon.

As used herein, the term "constitutional unit" refers to the repeating units that make up a polymer. For example, in the poly(vinylidene fluoride-co-hexafluoropropylene) of this invention the constitutional units are —$CF_2$—$CH_2$— and —$CF_2CF(CF_3)$—, which are derived from $CF_2$=$CH_2$, and $CF_2$=$CFCF_3$.

As used herein, "carbon-hydrogen bond capable of radical formation" refers to a constitutional unit of a polymer that has an extractable hydrogen atom such as, without limitation, the vinylidene fluoride constitutional unit shown above. The hydrogen atoms of the vinylidene fluoride constitutional unit will participate in the photoreduction of the triplet state of the UV-diradical forming entity to form a diradical, one radical being located on the constitutional unit and one on the diradical-forming entity. Collapse of this diradical will result in the formation of a covalent bond between the constitutional unit and the diradical forming species, which in turn is covalently bonded to a biobeneficial agent. The result is that the biobeneficial agent is secured to the surface of the outermost layer of the implantable medical device.

As used herein, "curing" refers simply to the act of covalent bond formation between the UV-active biobeneficial agent and a coating polymer of this invention.

When a UV-blocker is to be included in the drug reservoir layer, such may be accomplished in a number of ways. For instance, the UV-blocker may simply be dispersed in the coating formulation along with the polymer and any other excipients that might be included in the layer. Alternatively, the UV-sensitive therapeutic agent might be encapsulated in a micro- or nano-particle comprised of a polymer that either is constructed so as to itself absorb UV radiation at the therapeutic agent sensitive wavelengths or a separate UV-blocker can be incorporated in the particle-forming process so that the resultant particles include both therapeutic agent and UV-blocker dispersed therein. Any manner of particle may be used including, but not limited to, micelles, worm micelles, liposomes, polymerosomes, nano or mico shells, nano or micro spheres or simply solid nano or micro particles. When a core-shell structure is used, the UV-blocker will generally be encapsulated in the core along with the therapeutic agent. When a solid particle is used the UV-blocker may be dispersed throughout the particle or it can be bonded to the material of which the particle is constructed, usually a polymer.

As used herein, a "nanoparticle" refers to a solid having as its largest cross-sectional, i.e., through the solid as opposed to along its surface, dimension of no greater than 500, nanometers, preferably 250, nanometers and most preferably at present 100 nanometers. The solid can have a desired shape although substantially spherical particles are well-known in the art, are readily prepared and are presently preferred. By "substantially spherical" is meant that the particles need not have a surface that mimics a table tennis ball, i.e., virtually perfectly spherical but rather may by odd-shaped but would be considered generally "round" by one of skill in the art. The nanoparticle may be constructed of one or more biocompatible substances and may be porous so as to permit elution of the therapeutic substance embedded in it or may be biodegradable such that as the nanoparticle degrades the therapeutic substance is released into the environment.

A microparticle has the same characteristics as a nanoparticles except that its smallest cross-sectional dimension is greater than 500, nm.

A micelle is a spherical colloidal nanoparticle spontaneously formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in and when the solution is saturated with monomeric molecules then the CMC is reached, which forces remaining surfactant molecules to form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5, nm to about 50, nm, micelles have been shown to exhibit spontaneous accumulation in pathological areas with leaky vasculature and impaired lymphatic drainage, a phenomenon known as the Enhanced Permeability and Retention or EPR effect.

The problem with micelles formed from relatively low molecular weight surfactants is that their CMC is usually quite high so that the formed micelles dissociate rather rapidly upon dilution, i.e., the molecules head for open places at the surface of the water with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMCs as low as $10^{-6}$, M (molar). Thus, they tend to be very stable while at the same time showing the same beneficial characteristics as surfactant micelles. Any micelle-forming polymer presently known in the art or as such may become known in the future may be used in the method of this invention. Since micelles are nano-scale particles, they may be administered using the porous balloon discussed above as well as in polymeric matrices. Examples of micelle-forming polymers are, without limitation, methoxy poly(ethylene glycol)-b-poly(ε-caprolactone), conjugates of poly(ethylene glycol) with phosphatidylethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

In addition to the classical spherical micelles described above, therapeutic agents may be delivered using the methods of this invention in compositions comprising synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly(lactic acid), poly(ε-caprolactone), poly(ethylethylene) and polybutadiene. A representative description of worm micelle formation, characterization and drug loading can be found in Kim, Y., et al., *Nanotechnology*, 2005, 16:S484-S491. The techniques described there as well and any other that is currently known or may become known in the future may be used in the regional delivery method of this invention. In addition to compositions comprising micelles, therapeutic agents may be present in or on a delivery interface of this invention as a composition comprising liposomes.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)] sodium salt, 1,2-dimyristoyl-sn-glycero-3-[phospho-L-serine] sodium salt, 1,2-dioleoyl-sn-glycero-3-phosphoethanolamine-N-glutaryl sodium salt and 1,1',2,2', -tetramyristoyl cardiolipin ammonium salt.

Liposomes may be unilamellar, composed of a single bilayer, or they may be multilamellar, composed of two or more concentric bilayers. Liposomes range from about 20-100, nm diameter for small unilamellar vesicles (SUVs), about 100-5000 nm for large multilamellar vesicles and ultimately to about 100, microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

It has been reported that large unilamellar liposomes alone, that is, absent any additional therapeutic agent, when administered in large amounts intravenously may stimulate reverse cholesterol transport and may have anti-atherogenic effects similar to that of HDL. Williams, K. J., et al., *Arterioscler. Thromb. Vasc. Biol.*, 2000, 20:1033-39. While further evaluation is necessary, if such is proven to be the case, administration of large liposomes without added therapeutic agent using the delivery interface of this invention may provide a beneficial effect on patients known or suspected to be afflicted with a vascular disease.

The diblock copolymers discussed above with regard to micelle formation can be further modified to form bilayer structures similar to liposomes. The structures are referred to as polymerosomes. Depending on the length and chemical nature of the polymers in the diblock copolymer, polymerosomes can be substantially more robust that liposomes. In addition, the ability to control completely the chemical nature of each block of the diblock copolymer permits tuning of the polymerosome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymerosomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result is a polydispersion of micelles, worm micelles and vesicles of varying sizes. Polymerosomes can also be prepared by dissolving the diblock copolymer in a solvent and then adding a poor solvent for one of the blocks, which will result in the spontaneous formation of polymerosomes.

As with liposomes, polymerosomes can be used to encapsulate therapeutic agents by including the therapeutic agent in the water used to rehydrate the copolymer film. Polymerosomes can also be force-loaded by osmotically driving the therapeutic agent into the core of the vesicle. Also as with liposomes, the loading efficiency is generally low. Recently, however, a technique has been reported that provides polymerosomes of relative monodispersivity and high loading efficiency; generation of polymerisomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymerosomes on the concentric interfaces of the double emulsion. The actual polymerosomes are formed by completely evaporating the organic solvent from the shell. By this procedure the size of the polymerosomes can be finely controlled and, in addition, the ability to maintain complete separation of the internal fluids from the external fluid throughout the process allows extremely efficient encapsulation. This technique along with any other technique know in the art or as may become known in the future can be used to prepare a composition of therapeutic agents for use in or on a delivery interface of this invention.

When the UV-active biobeneficial agent is to be applied to the drug reservoir layer it may be desirable to clean the surface of the layer, which may have a monolayer of therapeutic agent disposed thereon as an artifact of the reservoir layer coating process. Should such be the case, the UV-active biobeneficial agent may, on curing, form covalent bonds with the therapeutic agent rather than a constitutional unit of the coating polymer. This might result in the biobeneficial agent being washed from the surface of the drug reservoir layer along with the therapeutic agent, which, if course, is intended to leave the device. To avoid or at least assuage this situation, the surface of the drug reservoir layer can be rapidly rinsed with a solvent for the therapeutic agent and rapidly dried to avoid more therapeutic agent blooming to the surface. By "rapidly" is meant as quickly as possible given the limitations of the equipment used to accomplish the task.

In the alternative, the surface may be subjected to an inert gas plasma such as, without limitation, an argon or a helium plasma to remove the therapeutic agent monolayer. Such is a technique for surface cleaning is well-known to those skilled in the art.

While many embodiments and alternatives have been described above with regard to the method of the present invention, it is understood that those skilled in the art will be able to recognize modifications, substitutions and additions to the method not expressly set forth herein. All such modifications, substitutions and additions are within the scope and spirit of this invention.

What is claimed:

1. A method, comprising:
   providing an implantable medical device comprising a device body;
   optionally disposing a primer layer over an exposed surface of the device body;
   disposing a drug reservoir layer over an exposed surface of the device body or, if opted for, over the primer layer, wherein:
   the drug reservoir layer comprises:
   a first polymer that includes at least one constitutional unit having a carbon-hydrogen bond capable of radical formation,
   a UV and/or visible light sensitive therapeutic agent; and
   optionally, a UV or visible light blocker that absorbs UV or visible radiation at the wavelength(s) to which the therapeutic agent is sensitive;
   optionally disposing a topcoat layer over the drug reservoir layer wherein the topcoat layer comprises a second polymer, which may be the same as or different than the first polymer, wherein
   the second polymer has at least one constitutional unit having a carbon-hydrogen bond capable of radical formation, wherein
   if the topcoat layer is opted for it optionally further comprises a UV or visible light blocker that absorbs UV or visible radiation at the wavelength(s) to which the therapeutic agent is sensitive;
   disposing a UV or visible light active biobeneficial agent over the drug reservoir layer or, if opted for, over the topcoat layer; and,
   curing the device with UV or visible radiation wherein:
   a covalent bond is formed between the UV light active biobeneficial agent and the first polymer or, if a top coat is opted for, the second polymer,
   wherein the UV or visible light active biobeneficial agent comprises a biobeneficial agent to which a UV or visible light radical-forming entity has been covalently bonded.

2. The method of claim 1, wherein the topcoat layer is not opted for and the surface of the drug reservoir layer is cleaned prior to disposition of the UV or visible light active biobeneficial agent.

3. The method of claim 2, wherein cleaning the drug reservoir layer comprises washing the surface of the drug reservoir layer with a solvent for the therapeutic agent followed immediately by drying.

4. The method of claim 2, wherein cleaning the drug reservoir layer comprises subjecting the surface of the drug reservoir layer to an inert gas plasma.

5. The method of claim 1, wherein the therapeutic agent is encapsulated in a micro- or nano- particle comprising the UV or visible light blocker.

6. The method of claim 1, wherein the first polymer constitutional unit comprises vinylidene fluoride.

7. The method of claim 6, wherein the first polymer comprises poly(vinylidene fluoride-co-hexafluoropropylene).

8. The method of claim 7, wherein the primer layer and the topcoat layer are not opted for.

9. The method of claim 8, wherein the UV and/or visible light sensitive therapeutic agent comprises an olimus drug.

10. The method of claim 9, wherein the olimus drug is selected from the group consisting of sirolimus, everolimus 40-O-(3-hydroxy)propylrapamycin, 40-[O-2-(2-hydroxy)ethoxy]ethylrapamycin, zotarolimus, 40-O-tetrazolerapamycin, 40-epi-(N1-tetrazole)rapamycin, biolimus A9, deforolimus, temsirolimus and AP23572 (Ariad Pharmaceuticals).

11. The method of claim 10, wherein the UV or visible light blocker is selected from the group consisting of carotene, tyrosine, phenyl alanine, dihydroxyphenylalanine, desaminotyrosine, vitamin A, a B vitamin, vitamin E, squalene, an aromatic steroid, retinoic acid, a tocopherol, retinol, retinol ester, carotinoids, anthocyanines, acetylsalicylic acid, benzoic acid, a benzoic acid ester, eosin, fluorescein, melanin, zinc oxide, titanium oxide, a metal and carbon black.

12. The method of claim 1, wherein the UV or visible light active biobeneficial agent is selected from the group consisting of UV or visible light active poly(ethylene glycol), poly (propylene glycol); poly(ethylene oxide-co-lactic acid);
poly(ethylene oxide), poly(propylene oxide); polyphosphazenes, phosphoryl choline, choline, poly(hydroxyethyl methacrylate), poly(hydroxypropyl methacrylate), poly(hydroxypropylmethacrylamide), poly(ethylene glycol) acrylate, 2-methacryloyloxyethylphosphorylcholine, n-vinyl pyrrolidone; poly(methacrylic acid), poly(acrylic acid), poly(alkoxymethacrylate), poly(alkoxyacrylate), poly(3-trimethylsilylpropyl methacrylate); poly(styrene-co-ethyene glycol), poly(isobutylene-co-ethylene glycol), poly(caprolactone-co-ethylene glycol), poly(lactide-co-ethyene glycol), poly(methyl methacrylate-co-ethylene glycol), poly(dimethylsiloxane-co-ethylene glycol), poly(vinylidene fluoride-co-ethylene glycol), poly(propylene oxide-co-ethylene glycol), poly(tetramethylene glycol), hydroxy functionalized poly(vinyl pyrrolidone), poly(ethylene glycol-block-butylene terephthalate), fibrin, fibrinogen, cellulose, starch, collagen, dextran, dextrin, hyaluronic acid, heparin, glycosaminoglycan, a polysaccharide, elastin, chitosan, alginate or combinations thereof.

13. The method of claim 11, wherein the UV or visible light active biobeneficial agent is selected from the group consisting of UV or visible light active poly(ethylene glycol), poly(propylene glycol); poly(ethylene oxide-co-lactic acid);
poly(ethylene oxide), poly(propylene oxide); polyphosphazenes, phosphoryl choline, choline, poly(hydroxyethyl methacrylate), poly(hydroxypropyl methacrylate), poly(hydroxypropylmethacrylamide), poly(ethylene glycol) acrylate, 2-methacryloyloxyethylphosphorylcholine, n-vinyl pyrrolidone; poly(methacrylic acid), poly(acrylic acid), poly(alkoxymethacrylate), poly(alkoxyacrylate), poly(3-trimethylsilylpropyl methacrylate); poly(styrene-co-ethyene glycol), poly(isobutylene-co-ethylene glycol), poly(caprolactone-co-ethylene glycol), poly(lactide-co-ethyene glycol), poly(methyl methacrylate-co-ethylene glycol), poly(dimethylsiloxane-co-ethylene glycol), poly(vinylidene fluoride-co-ethylene glycol), poly(propylene oxide-co-ethylene glycol), poly(tetramethylene glycol), hydroxy functionalized poly(vinyl pyrrolidone), poly(ethylene glycol-block-butylene terephthalate), fibrin, fibrinogen, cellulose, starch, collagen, dextran, dextrin, hyaluronic acid, heparin, glycosaminoglycan, a polysaccharide, elastin, chitosan, alginate and combinations thereof.

14. The method of claim 1, wherein the UV or visible light active radical-forming entity comprises an aryl ketone.

15. The method of claim 14, wherein the aryl ketone is selected from the group consisting of acetophenone, benzophenone, anthraquinone, anthrone, an anthrone-like heterocycle, a conjugated cyclic diketone, derivatives of any of the foregoing and combinations of any of the foregoing.

16. The method of claim 1, wherein the implantable medical device is a stent.

* * * * *